(12) United States Patent
Mohr et al.

(10) Patent No.: US 8,173,066 B2
(45) Date of Patent: May 8, 2012

(54) METHOD FOR IRRADIATING THROMBOCYTE CONCENTRATES IN FLEXIBLE CONTAINERS WITH ULTRA-VIOLET LIGHT

(75) Inventors: Harald Mohr, Hannover (DE); Wolfram H. Walker, Rödermark (DE)

(73) Assignees: Forschungsgemeinschaft der DRK Blutspendedienste e.V., Frankfurt (DE); Maco Pharma S.A., Mouvaux (FR)

( * ) Notice: Subject to any disclaimer, the term of this patent is extended or adjusted under 35 U.S.C. 154(b) by 532 days.

(21) Appl. No.: 12/086,806

(22) PCT Filed: Dec. 21, 2006

(86) PCT No.: PCT/DE2006/002311
§ 371 (c)(1),
(2), (4) Date: Nov. 20, 2008

(87) PCT Pub. No.: WO2007/076834
PCT Pub. Date: Jul. 12, 2007

(65) Prior Publication Data
US 2009/0155121 A1    Jun. 18, 2009

(30) Foreign Application Priority Data
Dec. 23, 2005 (DE) .................. 10 2005 062 410

(51) Int. Cl.
| | |
|---|---|
| A61L 2/00 | (2006.01) |
| G01N 21/00 | (2006.01) |
| G01N 23/00 | (2006.01) |
| C12N 13/00 | (2006.01) |
| A61M 31/00 | (2006.01) |
| A61M 37/00 | (2006.01) |
| A61B 19/00 | (2006.01) |

(52) U.S. Cl. .... 422/24; 422/1; 250/454.11; 250/455.11; 435/173.1; 604/56; 604/82; 604/83; 604/416

(58) Field of Classification Search ............... 422/1, 24; 250/454.11, 455.11; 435/173.1; 604/56, 604/82–83, 416
See application file for complete search history.

(56) References Cited

U.S. PATENT DOCUMENTS

| | | | |
|---|---|---|---|
| 4,469,227 A | 9/1984 | Faust | |
| 4,586,928 A | 5/1986 | Barnes et al. | |
| 4,952,812 A * | 8/1990 | Miripol et al. ........ | 250/455.11 |
| 4,952,818 A | 8/1990 | Erdelyi et al. | |
| 5,030,200 A | 7/1991 | Judy et al. | |
| 5,625,079 A | 4/1997 | Wollowitz et al. | |
| 6,268,120 B1 | 7/2001 | Platz et al. | |
| 6,686,480 B2 | 2/2004 | Wollowitz et al. | |
| 2001/0046450 A1 | 11/2001 | Laub et al. | |
| 2002/0138066 A1 | 9/2002 | Manica et al. | |
| 2003/0064001 A1 | 4/2003 | Fries et al. | |
| 2003/0072676 A1 | 4/2003 | Fletcher-Haynes et al. | |
| 2003/0228564 A1 | 12/2003 | Edrich et al. | |
| 2004/0186410 A1 | 9/2004 | Davidner et al. | |
| 2005/0202395 A1 | 9/2005 | Edrich et al. | |
| 2007/0164233 A1 | 7/2007 | Mohr | |
| 2010/0133203 A1 | 6/2010 | Walker et al. | |
| 2010/0178200 A1 | 7/2010 | Walker et al. | |

FOREIGN PATENT DOCUMENTS

| | | |
|---|---|---|
| CA | 2634296 | 7/2007 |
| DE | 29801590 | 4/1998 |
| DE | 102005062410 | 8/2007 |
| EP | 0542221 | 5/1993 |
| EP | 0727938 | 8/1996 |
| EP | 0933090 | 8/1999 |
| EP | 1002512 | 5/2000 |
| EP | 1308172 | 5/2003 |
| FR | 2887335 | 12/2006 |
| WO | WO 89/09067 | 10/1989 |
| WO | WO 95/12973 | 5/1995 |
| WO | WO 01/54738 | 8/2001 |
| WO | WO 01/54739 | 8/2001 |
| WO | WO 01/96340 | 12/2001 |
| WO | WO 02/26270 | 4/2002 |
| WO | WO 02/092806 | 11/2002 |
| WO | WO 03/063915 | 8/2003 |
| WO | WO 03/086479 | 10/2003 |
| WO | WO 03/090795 | 11/2003 |
| WO | WO 2004/032782 | 4/2004 |
| WO | WO 2004/033081 | 4/2004 |
| WO | WO 2005/089816 | 9/2005 |
| WO | WO 2005/089816 A1 * | 9/2005 |
| WO | WO 2006/136698 | 12/2006 |

(Continued)

OTHER PUBLICATIONS

Prodouz et al.; "Use of Laser-UV for Inactivation of Virus in Blood Products"; Blood, vol. 70, No. 2 (Aug. 1987); pp. 589-592; National Institutes of Health, Bethesda, MD.

Andreu et al.; "Ultraviolet irradiation of platelet concentrates: feasibility in transfusion practice"; Secteur d'Hemobiologie Transfusion, Paris, France, Jul. 17, 1989 pp. 401-406.

Derwood H. Pamphilon; "The Rationale and Use of Platelet Concentrates Irradiated With Ultraviolet-B Light"; Transfusion Medicine Reviews, vol. 13, No. 4(Oct. 1999); pp. 323-333.

Platelets Study Group; "Leukocyte Reduction and Ultraviolet B Irradiation . . . "; The New England Journal of Med.; Dec. 25, 1997 vol. 337, No. 26 pp. 1861-1869.

Kallenbach; "Inactivation of Viruses . . . "; Morgenthaler J-J(ed); Virus Inactivation in Plasma Products. Curr Stud Hematol Blood Transfus. Basel, Karger 1989, No. 56 pp. 70-82.

(Continued)

*Primary Examiner* — Jill Warden
*Assistant Examiner* — Monzer Chorbaji
(74) *Attorney, Agent, or Firm* — Locke Lord LLP; Alan B. Clement; Peter J. Fallon

(57) ABSTRACT

The invention relates to a method for inactivating pathogens such as bacteria and viruses and/or leucocytes in thrombocyte concentrations by irradiation in flexible containers with ultraviolet light using agitation. The blood product is packaged in a flexible bag to permit the intermixing of the fluid by agitation (tilting, rotation, translation). This is also promoted by the filling of the bag to a maximum 30% of the filling capacity.

31 Claims, No Drawings

FOREIGN PATENT DOCUMENTS

| | | |
|---|---|---|
| WO | WO 2007/076832 | 7/2007 |
| WO | WO 2008/034476 | 3/2008 |

OTHER PUBLICATIONS

Hart et al.; "Inactivation of Viruses during . . . "; Vox Sang 1993;64:82-88, S. Karger AG, Edinburgh, UK.

Chin; Virucidal Short Wavelength . . . Blood, vol. 86. No. 11 (Dec. 1, 1995): pp. 4331-4336.

International Search Report issued on Feb. 12, 2008, for International Application No. PCT/EP2008/004866.

Written Opinion of the International Searching Authority received Jan. 7, 2010 for International Application No. PCT/EP2008/004866.

Handbook of Transfusion Medicine, 4th Edition, Published 2007, Edited by DBL MCClelland, Scottish National Blood Transfusion Service, Edinburgh, Published by United Kingdom Blood Services, ISBN 0113226772.

* cited by examiner

METHOD FOR IRRADIATING THROMBOCYTE CONCENTRATES IN FLEXIBLE CONTAINERS WITH ULTRA-VIOLET LIGHT

The subject matter of the invention is a method for inactivating pathogens such as bacteria and viruses and/or leucocytes in platelet concentrates (thrombocyte concentrates, PCs) by irradiation with ultraviolet light.

It is known that the therapeutic application of blood preparations carries the risk that the recipients of the blood preparation are infected with viruses and bacteria. The viruses hepatitis B (HBV) and hepatitis C (HCV) and the Aids pathogens HIV 1 and HIV 2 are named by way of example. The risk always exists when, during the production of the preparation, no steps are taken to inactivate or eliminate the said pathogens.

Ultraviolet (UV) light is differentiated according to wavelength. In the context of this application, the following definition is applied: UVA: less than 400 to 320 nm, UVB: less than 320 to 280 nm and UVC less than 280 to 200 nm. It is known that by irradiation with short-wave ultraviolet (UV) light, i.e. in the wave length range below approximately 320 nm (UVB and UVC), viruses and also bacteria can be inactivated, for instance in blood plasma or in cellular blood preparations. Above 320 nm, the energy of the radiation is too low to inactivate microorganisms and viruses. Compared with chemical, photochemical and photodynamic methods of pathogen inactivation, mere irradiation with UV light essentially has the advantage of being effective on its own and not requiring the addition of reactive chemicals or photoactive substances.

Such additives or their split products or photo products frequently require subsequent removal, because they are toxic or mutagenic. In addition, they can cause the formation of neoantigenic structures in the treated preparation when they bind to plasma proteins and cell surfaces. Generally, such additives are not able to be removed completely; at least, their removal requires additional effort. Such additional working steps can, moreover, impair the quality of the sterilised preparations. UVC is the most effective for direct pathogen inactivation. However, it has the disadvantage that it only penetrates protein-containing solutions such as blood plasma or turbid suspensions (e.g. PCs) up to a very small penetration depth.

UVC was used during the Second World War and also shortly thereafter to sterilise blood plasma and albumin solutions, especially in order to inactivate hepatitis viruses. At that time, one proceeded so that the solution was directed in a through-flow apparatus as a thin film past a UVC light source. The method proved to be not sufficiently reliable and was abandoned (Kallenbach N R, Cornelius P A, Negus D, et al. Inactivation of viruses by ultraviolet light. Curr Stud Hematol Blood Tranfus 1989, 56, 70-82).

In the present day, methods are used which have been further developed, operating according to the same principle, in order to sterilise therapeutic plasma protein preparations. In all cases the concern was or is with treating larger volumes, i.e. plasma pools or protein solutions up to several hundred litres and even more (Hart H, Reid K, Hart W. Inactivation of viruses during ultraviolet light treatment of human intravenous immunoglobulin and albumin. Vox Sang 1993; 64(2): 82-8, and Chin S, Williams B, Gottlieb P, et al. Virucidal short wavelength ultraviolet light treatment of plasma and factor VIII concentrate: protection of proteins by antioxidants; Blood 1995; 86(11):4331-6).

For sterilising a plurality of individual units of PCs, which have been obtained from blood donations or by mechanical apheresis—with a volume of at most up to several hundred ml—the aforementioned through-flow apparatus are not suitable. However, this is in fact necessary in the daily practice of a blood bank.

UVB is likewise microbiocidal and virucidal, although not to the same extent as UVC. It penetrates protein-containing solutions and turbid suspensions somewhat better than UVC, but its penetration depth, e.g. in plasma or PCs, can also only be established in the range of a few millimeters. Irradiation with UVB was tested, in order to inactivate T-lymphocytes in PCs, which are considerably more UV-sensitive than viruses or bacteria. Hereby, an allo-immunisation against exogenous HLA antigens in the recipients of the preparations is to be prevented, which can cause the recipients to become refractory against further transfusions of PCs (Andreu G, Boccaccio C, Lecrubier C, et al. Ultraviolet irradiation of platelet concentrates: feasibility in transfusion practice. Transfusion 1990; 30(5):401-6 and Pamphilon D H. The rationale and use of platelet concentrates irradiated with ultraviolet-B light. Transfus Med Rev 1999; 13(4):323-33).

In fact, the method did not win through, because the leucocyte filtration, which was developed at almost the same time, constitutes an alternative which is similarly effective but is more favourable from the point of view of cost and effort (Leukocyte reduction and ultraviolet B irradiation of platelets to prevent alloimmunization and refractoriness to platelet transfusions. The Trial to Reduce Alloimmunization to Platelets Study Group. N Engl J Med 1997; 337(26):1861-9).

It was likewise described that viruses in platelet suspensions can be inactivated by irradiation with monochromatic UVB light (wavelength 308 nm). An excimer laser was used here; the test volume was a few ml (Prodouz K N, Fratantoni J C, Boone E J, Bonner R F. Use of laser-UV for inactivation of virus in blood products. Blood 1987; 70(2):589-92). Clearly, one did not depart beyond this benchmark. In fact, no method is known from the literature by which viruses or bacteria in complete PCs can be decontaminated exclusively by irradiation with UV light (i.e. UVB or UVC).

PCs are obtained by mechanical thrombapheresis from individual donors or else are isolated from blood donations, with the platelets from several blood donations (generally 4-6) being pooled. The volume of the PC which is able to be obtained accordingly generally lies between approximately 200 and 350 ml. However, PCs are also produced from individual blood donations, the volume of which is correspondingly smaller (between approximately 40 and 80 ml). Both in pool PCs and also in apheresis PCs, the platelets are either suspended in blood plasma or in special storage media with a residual plasma content of approximately 30 to 40%. The PCs are stored in flat gas-permeable plastic bags at 20-24° C.

It would be desirable to sterilise PCs in such bags with UV light. Indeed, the problem which has been mentioned exists here, namely that the preparations are almost impenetrable by UV light. This is to be clarified by the following calculation example: if UVB is provided for sterilisation and one assumes a PC volume of approximately 300 ml, in addition a penetration depth of the UVB radiation of 1 mm and exposure of both sides of the bag, a suitable exposure bag would have to have a surface of at least 1500 $cm^2$.

It appears to be difficult, if not precluded, to routinely process larger quantities of bags having such dimensions. The problem becomes even significantly greater if, instead of with UVB, one wishes to sterilise the PCs with UVC, because its penetration depth is much less.

Surprisingly, it was found that the above problem is solved by a method according to Claim 1. Preferred embodiments are the subject matter of the dependent claims or are described below.

According to the present invention, the PCs are moved in a suitable manner in their exposure bags. The movement takes place here so vigorously that layers form in areas inside the PCs, these layers being so thin that they can be penetrated by the UV radiation. At the same time, the movement must be such that the PC suspensions are efficiently mixed in the bags. Both are to be realized when the following conditions exist:

1. The exposure bags are highly flexible and they are not fixed during the exposure, e.g. clamped between quartz plates. They therefore adapt themselves to every change in form of the PC suspension, which occurs when the bags are moved.
2. The movement of the bags takes place either horizontally (linearly in a back-and-forth direction or in circular or ellipsoid shape) or else vertically (rocked).
3. The exposure bags are filled to a maximum of 30%, in particular to a maximum of 20% of their maximum filling volume.

In all cases, the reversal of the direction of movement is to be so abrupt that the majority of the PC suspension moves further into the original direction, as a result of its inertia, and therefore the residue which remains behind can form a thin layer which is penetrable by the UV radiation. In connection with the constant intermixing due to the movement of the bags during irradiation, finally the entire PC (and the viruses and/or bacteria contained therein) is exposed to the UV radiation. The PCs are thereby sterilised.

The exposure bags are made from UV-transparent plastic material. Suitable plastics are, for example, ethylene vinyl acetate and polyolefins with sheet thicknesses of 1 mm and less, in particularly sheet thickness less than 0.5 mm. The exposure bags are constructed so as to be flat and preferably have no absorption maxima in the range of 200 to 320 nm. In the horizontal filled state, the exposure bags are only a few mm thick, e.g. less than 10 mm and in particular less than 5 mm, preferably even less than 3 mm and they are intended to hold specimen volumes of for example up to 200 or up to 300 ml. The maximum holding capacity (volume) of the exposure bag is, however, greater by at least factor 3, generally by at least 5 times, preferably at least 10 or even at least 20 times greater than the actual specimen volume contained in it, which is to be treated.

EXPERIMENTAL INVESTIGATIONS

The described experiments illustrate the efficacy of the method and are not limited to the inactivation of the undermentioned bacteria and/or viruses. There is also no limitation to "random donor" PCs, which were used in the described experiments, and the method according to the invention is also able to be used on thrombapheresis preparations. All the experiments were carried out three to six times. The indicated results represent in each case the mean values±standard deviation.

Platelet Concentrates

The PCs were produced from pools of respectively 5 buffy coats, which in turn originated from regular blood donations. The PCs had a volume of approximately 300 to 350 ml; the platelet concentration was approximately $10^9$/ml. The platelets were suspended in storage medium SSP+(product of the company MacoPharma). The residual plasma content was approximately 30 to 40%.

Bacteriological Investigations

The following strains of bacteria were used in the inactivation experiments:
Staphylococcus (S.) epidermis
Staphylococcus (S.) aureus
Bacillus (B.) cereus
Klebsiella (K.) pneumoniae.

Concentrations of bacteria were determined by means of a colony formation assay and are expressed as colony forming units (CFU)/ml. In the experiments for inactivation of bacteria, complete PCs or PC aliquots were spiked with $10^4$ to $10^5$ CFU/ml of one of the indicated species and then irradiated with UV light.

Virological Investigations

PC aliquots were spiked with suid herpes virus (SHV-1, pseudorabies virus, Aujeszky strain) or vesicular stomatitis virus (VSV, Indiana strain). Virus titers were determined by means of CPE assay (CPE=cytopathic effect). They are indicated as $TCID_{50}$ (TCID=tissue culture infective dose). Vero cells served as indicator cells. The initial virus concentration in the experiments which were carried out was approximately $10^5$ to $10^7$ $TCID_{50}$.

Exposure Apparatus

One of the two exposure apparatus used was equipped with tubes which emitted UVB light. The irradiation took place from both sides of the exposure bags which were put in place, i.e. from above and from below. The exposure apparatus was provided with a shaking device which carried out back-and-forth movements at a frequency of 60 changes of direction/min. A second exposure apparatus was likewise equipped with tubes which emitted UVB light. The irradiation likewise took place from both sides. A third apparatus (of the same type of construction as the second) was provided with tubes which emitted UVC light (wavelength: 254 nm). Both apparatus were able to be provided with 2 different shaking devices: one horizontal shaker, which carried out ellipsoid back-and-forth movements, and a rocking shaker.

Exposure Bags

The exposure bags which were used consisted of ethylene vinyl acetate (EVA), which is penetrable by UV light. Two sizes of bags were used:
1. 14.5×18.5 cm (external bag area approx. 268 cm$^2$)
2. 22.5×38 cm (external bag area approx. 855 cm$^2$)

In the experiments with the small EVA bags, the sample volume was 80 ml, in those with the large bags approximately 300-350 ml (complete PCs were treated).

Experiment Example 1

Inactivation of S. epidermidis by UVB, with and without Free Movement of the Platelet Suspension During Shaking In the experiment, the sample volume was 80 ml. The free mobility of the platelet suspension during shaking, and hence the formation of a thin layer was prevented in a sample in that the exposure bags were clamped securely between two quartz plates. The resulting layer thickness was approximately 3 mm. In the second sample, the distance between the quartz plates was increased such that the platelet suspension was largely able to move freely during shaking. The two samples were irradiated with 1 J/cm$^2$.

As Table 1 shows, the bacteria titer in the fixed samples was reduced by approximately 2 $\log_{10}$, but by more than 4 $\log_{10}$ in the loosely placed ones.

TABLE 1

| Sample title | Bacteria titer($\log_{10}$ CFU/ml) |
| --- | --- |
| Untreated control | 4.1 ± 0.03 |
| Securely clamped sample | 1.4 ± 1.29 |
| Loosely placed sample | −0.40 ± 0.35 |

Experiment Example 2

Inactivation of S. epidermidis by UVB in Complete PCs, Loosely or Securely Clamped Exposure Bags, with Shaking The PC volume in this experiment was 330 ml, the average layer thickness in large EVA bags was accordingly approximately 3.9 mm. The PCs were irradiated with 3 UVB doses (0.8, 1.0 and 1.2 J/cm$^2$) under the following conditions:
1. without shaking, loosely placed between quartz plates
2. with shaking, pressed between quartz plates.

As the experiment results show (Table 2), in the PCs which were securely clamped during shaking, the bacteria titer was reduced by the UVB treatment by up to approximately 2 $\log_{10}$, by comparison in the loosely placed samples, depending on the dose, by approximately 3.4 to more than 4 $\log_{10}$.

TABLE 2

| Sample placement | UVB Dose(J/cm$^2$) | Bacteria Titer ($\log_{10}$ CFU/ml) |
| --- | --- | --- |
| shaken, securely clamped | 0 | 4.11 ± 0.00 |
| shaken, securely clamped | 0.8 | 2.14 ± 0.48 |
| shaken, securely clamped | 1.0 | 1.95 ± 0.03 |
| shaken, securely clamped | 1.2 | 1.99 ± 0.03 |
| shaken, loose | 0 | 4.19 ± 0.11 |
| shaken, loose | 0.8 | 0.77 ± 0.69 |
| shaken, loose | 1.0 | −0.14 ± 0.05 |
| shaken, loose | 1.2 | −0.40 ± 0.05 |

Experiment Example 3

Inactivation of Further Bacteria in Freely Movable or Fixed PC Aliquots by UVB

It can be seen from the first two experiment examples that S. epidermidis is effectively inactivated in PCs under the condition that the PC suspension can move freely during the UV irradiation. In the following experiment, the following additional strains of bacteria were tested: S. aureus, B. cereus and K. pneumoniae.

The conditions were the same as described in Experiment Example 1. In all three cases a similar result as with S. epidermidis: in the loosely placed PC samples, the bacteria were inactivated by approximately 3.9 to 4.29 $\log_{10}$, whereas the titers in the fixed samples were only reduced by approximately 2 to 3.4 $\log_{10}$ (Table 3).

TABLE 3

| Strain of bacteria | Sample Title | Bacteria Titer ($\log_{10}$ CFU/ml) |
| --- | --- | --- |
| S. aureus | untreated control | 4.88 ± 0.00 |
| S. aureus | securely clamped, shaken | 1.49 ± 1.30 |
| S. aureus | loosely placed, shaken | 0.97 ± 0.86 |
| B. cereus | untreated control | 4.99 ± 0.09 |
| B. cereus | securely clamped, shaken | 2.99 ± 0.13 |
| B. cereus | loosely placed, shaken | 0.74 ± 0.68 |
| K. pneumoniae | untreated control | 4.94 ± 0.08 |
| K. pneumoniae | securely clamped, shaken | 2.34 ± 0.24 |
| K. pneumoniae | loosely placed, shaken | 1.00 ± 0.89 |

Experiment Example 4

Inactivation of S. epidermidis in PC Aliquots by UVB Under Various Shaking Conditions An investigation was carried out as to whether the inactivation of S. epidermidis in loosely placed PC aliquots is also increased when different horizontal shakers are used from the one used in Experiments 1 to 3, which, as mentioned, makes back-and-forth movements. In the following experiments, an orbital shaker was used which carried out a circular movement (radius: 3 cm, rotation rate: 50/min), in addition a rocker with 50 up- and down movements per minute. Again, one of the two samples (80 ml) was clamped securely between quartz plates, the other was placed loosely. As can be seen from the results shown in Table 4, this time the extent of the bacteria inactivation was higher by 3 to 4 $\log_{10}$ in the loosely placed PC samples than in the securely clamped ones.

TABLE 4

| Shaker | Sample Title | Bacteria Titer ($\log_{10}$ CFU/ml) |
| --- | --- | --- |
| — | untreated control | 4.94 ± 0.16 |
| Orbital | securely clamped | 4.23 ± 0.00 |
| Orbital | loosely placed | 0.50 ± 0.39 |
| Rocker | securely clamped | 4.02 ± 0.17 |
| Rocker | loosely placed | 0.87 ± 0.78 |

Experiment Example 5

Inactivation of Suid Herpes Viruses by UVB, without or with Free Movement of the PC Aliquots During Shaking In order to test whether the increase of inactivation of pathogens in PCs which are not fixed during irradiation with UV light, relates not only to bacteria but also to viruses, the following experiment was carried out: PC aliquots of 80 ml were spiked with suid herpes viruses (SHV-1) and were treated with UVB as described in Experiment Example 1. In the freely placed samples, the virus titer was reduced by almost 4 $\log_{10}$, in the securely clamped samples, on the other hand, only by approximately 3 $\log_{10}$. This confirms that under the said conditions, the inactivation of viruses is also distinctly improved.

TABLE 5

| Sample Title | Virus Titer ($\log_{10}$ TCID$_{50}$) |
| --- | --- |
| untreated control | 4.4 ± 0.2 |
| securely clamped sample | 1.41 ± 0.18 |
| loosely placed sample | 0.56 ± 0.15 |

Experiment Example 6

Inactivation of Vesicular Stomatitis Viruses by UVB, without or with Free Movement of the PC Aliquots During Shaking The experiment was carried out as described in Experiment Example 5, except that the PC aliquots were spiked with VSV instead of with SHV-1. Again, the extent of the virus inactivation in the loosely placed samples was greater by more than 6.46 $\log_{10}$ than in the comparative samples, which were fixed between quartz plates during exposure (Table 6). It is, in fact, noticeable that also in these, the virus titer was relatively greatly reduced (by approximately 5.4 $\log_{10}$). VSV is clearly more UV-sensitive than SHV-1.

TABLE 6

| Sample Title | Virus Titer ($Log_{10}$ $TCID_{50}$) |
|---|---|
| untreated control | 6.7 ± 1.05 |
| securely clamped sample | 1.29 ± 1.05 |
| loosely placed sample | ≦0.24 ± 0.00 |

Experiment Example 7

Inactivation of *S. epidermidis* by UVC, without or with Free Movement of the PC Aliquots During Shaking In this experiment, the irradiation took place with UVC instead of UVB. The UV dose was 0.3 $J/cm^2$ (exposure time: 60 sec). Otherwise, the conditions were as described in Experiment Example 1. As can be seen from Table 7, the bacteria titer in the fixed samples was only reduced by approximately 1 $\log_{10}$. This clearly reflects the small penetration depth of UVC into the platelet suspension. In the loosely placed samples, on the other hand, no more bacteria were able to be found; the inactivation factor was greater than 4 $\log_{10}$.

TABLE 7

| Sample Title | Bacteria Titer ($\log_{10}$ CFU/ml) |
|---|---|
| untreated control | 4.08 ± 0.04 |
| securely clamped sample | 2.99 ± 0.13 |
| loosely placed sample | ≦0.24 |

Experiment Example 8

Inactivation of VSV by UVC, without or with Free Movement of the PC Aliquots During Shaking As in Experiment Example 6, VSV was used as the test virus. The conditions were the same as in Experiment Example 7. The results shown in Table 8 show that also in this case, the extent of pathogen inactivation was much more marked in the loosely placed samples than in the fixed ones: whereas the virus titer in the latter was only reduced by approximately 1.5 $\log_{10}$ it was approximately 6.2 $\log_{10}$ in the non-fixed samples.

TABLE 8

| Sample Title | Virus Titer ($Log_{10}$ $TCID_{50}$) |
|---|---|
| untreated control | 6.92 ± 0.22 |
| securely clamped sample | 5.47 ± 0.21 |
| loosely placed sample | 0.74 ± 0.76 |

The invention claimed is:

1. A method for inactivating pathogens and/or leucocytes in platelet concentrates (PCs) comprising the steps:

providing PCs obtained from donor blood and/or by mechanical apheresis, exposing the PCs to irradiation with ultraviolet (UV) light, in which the PCs consist of a plurality of units which are able to be handled individually and stored separately, and the PC units are each placed in flexible, UV-penetrable flat exposure bags, wherein the exposure bags are filled to less than 30% of the maximum filling volume of the exposure bags and the exposure bags are moved during the irradiation with UV light so that the contents of the exposure bags are circulated and zones of changing layer thicknesses are formed by the movement, said ultraviolet light having UVC with a wavelength of about 200 nm to less than about 280 nm and having a light energy of about 0.01 to about 2 $J/cm^2$.

2. The method according to claim 1, wherein the pathogens are viruses and/or bacteria.

3. The method according to claim 1, wherein through the movement, the zones have irradiated regions for which regularly at times layer thicknesses below 1 mm are given.

4. The method according to claim 1, wherein the movement, in particular the amplitude of the movement, takes place so that within the PCs irradiated regions are formed in which the layer thickness is regularly at times less than 0.5 mm.

5. The method according to claim 1, wherein the exposure bags have an underside and an upper side and the sum of the areas of the underside and the upper side, which is or can be in contact with the bag content, is more than 90 area percent.

6. The method according to claim 1, wherein the ultraviolet light contains UVB irradiation having a wavelength of less than about 320 to about 280 nm.

7. The method according to claim 1, wherein each unit is produced from samples up to a maximum of 8 donors.

8. The method according to claim 7, wherein there is maximum of 6 donors.

9. The method according to claim 1, wherein each unit originates from one donor.

10. The method according to claim 1, wherein the PC contains at least $1\times10^8$ platelets per ml.

11. The method according to claim 10, wherein the PC contains at least $5\times10^8$ platelets per ml.

12. The method according to claim 1, wherein the irradiation with UVB takes place with a light energy of about 0.3 to 5 $J/cm^2$.

13. The method according to claim 12, wherein the irradiation with UVB takes place with a light energy of about 0.5 to 2.5 $J/cm^2$.

14. The method according to claim 12, wherein the exposure bags have an average filling level of about less than 5 mm, and through the movement wave troughs are constantly produced which have layer thicknesses of less than 1 mm.

15. The method according to claim 14, wherein the thickness is less than 0.1 mm.

16. The method according to claim 1, wherein the irradiation with UVC takes place with a light energy of about 0.1 to about 1 J/cm$^2$.

17. The method according to claim 1, wherein the PCs contain plasma and if applicable a suitable storage medium, in which the plasma content is greater than about 20% by weight.

18. The method according to claim 1, wherein the PCs contain a buffered aqueous storage medium.

19. The method according to claim 1, wherein viruses, bacteria and/or leucocytes are inactivated and the function of the platelets remains substantially unchanged.

20. The method according to claim 1, wherein the exposure bags have a volume of up to 5000 ml.

21. The method according to claim 1, wherein the exposure bags are held so as to be movable in the apparatus in which they are moved and irradiated, and are not clamped between two surfaces, wherein said surfaces are UV-penetrable glass or plastic plates.

22. The method according to claim 1, wherein the exposure bags are moved during at least three quarters of the total exposure duration.

23. The method according to claim 1, wherein the exposure bags are moved by shaking.

24. The method according to claim 1, wherein the exposure bags are moved by rocking.

25. The method according to claim 1, wherein the exposure bags are moved by rotation.

26. The method according to claim 1, wherein the shaking takes place with an orbital shaker, platform shaker, rocker shaker or tumbler shaker.

27. The method according to claim 1, wherein the exposure bags are placed on one side so that during and by the movement or shaking, the height of the exposure bag, viewed in relation to the distance along the surface normal between the surface on which the exposure bags lie, and the point of intersection with the upper surface of the exposure bag over the entire upper surface of the exposure bag which is in contact with the bag contents changes constantly.

28. The method according to claim 1, wherein the exposure bags have an average filling level of about 10 mm, and through the movement wave troughs are constantly produced which have layer thicknesses of less than half of the mean filling level.

29. The method according to claim 1, wherein during the exposure, the exposure bags are moved constantly with an amplitude of about 0.2 to about 8 cm at least in the x-direction and if applicable also in the y-direction and independently therefrom, the frequency of the change in direction of the shaking movement is 0.5 to 10 Hz.

30. The method according to claim 1, wherein during the exposure, the exposure bags are filled to a maximum of 20% of their maximum filling volume.

31. The method according to claim 1, wherein the exposure bags have an underside and an upper side and the sum of the areas of the underside and the upper side, which is or can be in contact with the bag content, is more than 99 area percent.

* * * * *